(12) United States Patent
Lee et al.

(10) Patent No.: US 7,767,705 B2
(45) Date of Patent: Aug. 3, 2010

(54) COMPOUNDS THAT INHIBIT TRPV1 AND USES THEREOF

(75) Inventors: Chih-hung Lee, Vernon Hills, IL (US); Richard J Perner, Gurnee, IL (US); Brian S. Brown, Evanston, IL (US); John Darbyshire, Allschwil (CH)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 11/844,712

(22) Filed: Aug. 24, 2007

(65) Prior Publication Data

US 2008/0058401 A1    Mar. 6, 2008

Related U.S. Application Data

(60) Provisional application No. 60/840,254, filed on Aug. 25, 2006.

(51) Int. Cl.
*A61K 31/416* (2006.01)
*C07D 231/56* (2006.01)

(52) U.S. Cl. .................................. 514/405; 548/361.1

(58) Field of Classification Search ................. 514/405; 548/361.1
See application file for complete search history.

(56) References Cited

U.S. PATENT DOCUMENTS

| | | | |
|---|---|---|---|
| 3,043,694 A | 7/1962 | Barr et al. | |
| 3,647,819 A | 3/1972 | Kirchner et al. | |
| 3,711,610 A | 1/1973 | Kirchner et al. | |
| 3,814,711 A | 6/1974 | Eloy et al. | |
| 4,958,026 A | 9/1990 | Schoellkopf et al. | |
| 5,362,878 A | 11/1994 | Chang et al. | |
| 5,444,038 A | 8/1995 | James et al. | |
| 5,646,140 A | 7/1997 | Sugg et al. | |
| 5,656,634 A | 8/1997 | Chang et al. | |
| 5,760,246 A | 6/1998 | Biller et al. | |
| 6,001,860 A | 12/1999 | Hamanaka | |
| 6,291,476 B1 | 9/2001 | Kordik et al. | |
| 6,472,414 B1 | 10/2002 | Biller et al. | |
| 6,511,998 B2 | 1/2003 | Kordik et al. | |
| 6,555,539 B2 | 4/2003 | Reich et al. | |
| 6,743,793 B2 | 6/2004 | Torisu et al. | |
| 6,858,577 B1 | 2/2005 | Zhang et al. | |
| 6,933,311 B2 | 8/2005 | Lee et al. | |
| 7,084,176 B2 | 8/2006 | Morie et al. | |
| 2004/0157849 A1 | 8/2004 | Lee et al. | |
| 2004/0259912 A1 | 12/2004 | Matsumoto et al. | |
| 2005/0119304 A1 | 6/2005 | Yura et al. | |

FOREIGN PATENT DOCUMENTS

| | | |
|---|---|---|
| EP | 0013411 | 7/1980 |
| EP | 0418071 | 9/1990 |
| EP | 0609960 | 9/1990 |
| EP | 0418071 | 3/1991 |
| EP | 0587180 | 9/1993 |
| EP | 1256574 | 2/2001 |
| EP | 1403255 | 6/2002 |
| EP | 1437344 | 7/2004 |
| FR | 01344579 | 12/1962 |
| FR | 1344579 | 10/1963 |
| GB | 2020280 | 4/1979 |
| JP | 625001687 | 1/1987 |
| JP | 62116559 | 5/1987 |
| JP | 1031766 | 2/1989 |
| JP | 1087629 | 3/1989 |
| JP | 2001122895 | 5/2001 |
| WO | 9113874 | 9/1991 |
| WO | WO 9113874 | 9/1991 |
| WO | 9726240 | 7/1997 |
| WO | 9850347 | 11/1998 |
| WO | 0050387 | 8/2000 |
| WO | 0208221 | 1/2002 |
| WO | 03014064 | 2/2003 |
| WO | 03022809 | 3/2003 |
| WO | 03049702 | 6/2003 |
| WO | 03053945 | 7/2003 |
| WO | 03055484 | 7/2003 |
| WO | 03055848 | 7/2003 |
| WO | 03070247 | 8/2003 |
| WO | 03080578 | 10/2003 |
| WO | 03097586 | 11/2003 |
| WO | 2005028445 | 3/2005 |
| WO | WO 2005 028445 | * 3/2005 |

OTHER PUBLICATIONS

Stella, Valentino J, Expert Opinion of Therapeutic Patents, Prodrugs as therapeutics, 2004 14(3): 277-280.*

(Continued)

*Primary Examiner*—Kamal A Saeed
*Assistant Examiner*—Samantha L Shterengarts
(74) *Attorney, Agent, or Firm*—Lisa V. Mueller; Polsinelli Shughart PC

(57) ABSTRACT

Compounds of formula (I)

(I)

wherein $R_3$, $R_7$, $R_9$ and L are defined in the description are TRPV1 antagonists that exhibit low inhibitory activity against CYP3A4. Compositions comprising such compounds and methods for treating conditions and disorders using such compounds and compositions are also disclosed.

7 Claims, No Drawings

OTHER PUBLICATIONS

Wolff et al. (Burger's Medicinal Chemistry, 5th Ed., vol. 1, pp. 975-977, 1994).*

Testa, Bernard, Biochemical Pharmacology, Prodrug Research: futile or fertile? 68 (2004) 2097-2106.*

Ettmayer, Peter, Medicinal Chemistry, Lessons Learned from Marketed and Investigational Prodrugs, 47(10) (2004) 2394-2404.*

Drizin, Irene. Structure-activity studies of a novel series of 5,6-fused heteroaromatic ureas as TRPV1 antagonists. Bioorganic and Medicinal Chemistry. 14 (2006) 4740-4749.*

Remington, Joseph P., The Science and Practice of Pharmacy, 20th Ed. (2000), 218-220.*

Adams, et al., "Dialkylaminoalkylquinolines," J. Chem. Soc. (1957), pp. 3066-3071.

Berge, et al. "Pharmaceutical Salts," Journal of Pharmaceutical Sciences, vol. 66, No. 1 et seq. (1977).

Cannon, et al., "Synthesis of N-alkyl derivatives of 4-(2'-aminothyl)indole," J. Heterocyclic Chemistry, vol. 19 (1982), pp. 1195-1199.

Caterina, et al., "Impaired Nociception and pain sensation in mice lacking the capsaicin receptor," Science, vol. 288, (2000), pp. 306-313.

Caterina, et al., "The capsaicin receptor: a heat-activated ion channel in the pain pathway," Nature, vol. 389 (1997), pp. 816-824.

Caterina, et al., "The Vanilloid Receptor: A Molecular gateway to the pain pathway," Annual Review of Neuroscience vol. 24 (2001), pp. 487-517.

Collier, et al., Br. J. Pharmacol. Chemother, vol. 32 (1968), pp. 295-310.

Craig, et al., "Derivatives of aminoisoquinolines," J. Am. Chem. Soc., vol. 64 (1942), pp. 783-784.

Davies, "Indazole Derivatives: The synthesis of various amino- and hydroxy-indazoles and erived slphonic acids," J. Chem. Soc. (1955), pp. 2412-2423.

Davis, et al., "Vanilloid receptor-1 is essential for inflammatory thermal hyperalgesia," Nature, vol. 405 (2000) pp. 183-187.

Drizin, et al., "Structure-activity studies of a novel series of 5,6-fused heteroaromatic ureas as TRPV1 antagonists," Bioorganic & Med. Chem., vol. 14 (2006), pp. 4740-4749.

Fieser, et al., "A comparison of heterocyclic systems with benzene. VI. Quinines of the quinoline and isoquinoline series," J. Amer. Chem. Soc. 57:1840-1844 (1935).

Forbes, et al., "N-(1-methyl-5-indolyl)-N'-(3-pyridyl)urea hydrochloride: the first selective 5-HT1C receptor antagonist," J. Med. Chem., vol. 36 (1993), pp. 1104-1107.

Fowler, et al., "Intravesical treatment of overactive bladder," Urology, vol. 55, No. Supp 5A (2000), pp. 60-64.

Gall, et al., "171. On a few derivatives of heterocyclic carbonic acids IV. Metal ions and biological action, 36th report," Helv. Chim. Acta, vol. 37 (1954), pp. 9094. Translation.

Gall, et al., "171. On a few derivatives of heterocyclic carbonic acids IV. Metal ions and biological action, 36th report," Helv. Chim. Acta, vol. 38, No. 171 (1955), pp. 1421-1423. Translation.

Giencke, et al. "Desmethyl(trifluormethyl)actinomycine," Liebigs Ann. Chem., vol. 6 (1990), pp. 569-579.

Hayes, et al., "Cloning and functional expression of a human orthologue of rat vanilloid receptor-1," Pain, vol. 88 (2000), pp. 205-215.

Honma, et al., "Structure-based generation of a new class of potent Cdk4 inhibitors: New de Novo design strategy and library design," J. Med. Chem., vol. 44 (2001), pp. 4615-4627.

Iupac 1974 Recommendation for Section E, Fundamental Sterochemistry, Pure App. Chem., vol. 45 (1976), pp. 13-30.

Kawasaki, et al., "A new approach to 4-(2-aminoethyl)indoles via Claisen ortho-amide rearrangement of 3-hydroxy-2-methoxyindolines," J. Chem. Soc. Chem. Commun., vol. 10 (1990), pp. 781-782.

Kumar, et al. "Antiparasitic agents: Part XV—synthesis of 2-substituted 1(3)H-imidazo[4,5-f]isoquinolines as anthelmintic agents," Indian Journal of Chemistry, vol. 31B (1992), pp. 177-182.

Landsiedel-Maier, "Structure Activity Relationship of Homonchiral 7-Substituted 1-Aminoindans as 5-HT1A Receptor Ligands," Archly Der Pharmazie, vol. 331 (1998), pp. 59-71.

Lichtenthaler, et al., "Nucleosides. 44. Benzo-separated Pyrazolopyrimidines: Expeditions Synthesis of [3,4-g] and [3,4-h]-linked Pyrazoloquinazolinones" Tetrahedron Letters, vol. 22, No. 44 (1981), pp. 4397-4400.

Lila et al., "Large scale preparation of protected 4-aminomethylbenzamidine. Application to the synthesis of the thrombin inhibitor, melagatran," Synth. Comm., vol. 28 (1998), pp. 4419-4429.

Mooney, et al., "Potential antitumor agens, 10. Synthesis and biochemical properties of 5-N-alkylamino-,N,N-dialkylamino-, and N-alkylacetamido-1-formylisoquinoline thiosemicarbazones," Journal of Medicinal Chemistry, vol. 17, No. 11 (1974), pp. 1145-1150.

Mukkala, et al., "124. New heteroromatic complexing agents and luminescence of their europium (III) and terbium(III) chelates," Helvetica Chima Acta, vol. 75 (1992), pp. 1621-1632.

Naruto, et al., "Photo-induced Friedel-Crafts reactions. Iv> Indoleacetic acids," Chemical and Pharmaceutical Bulletin, Tokyo, vol. 20, No. 10 (1972), pp. 2163-2171.

Nolano, et al., "Topical capsaicin in humans: parallel loss of epidermal nerve fibers and pain sensation," Pain, vol. 81 (1999), pp. 135-145.

Nunn, et al., "Semmler-Wolf Aromatization and Abnormal Beckmann and Schmidt Reactions of 3-Alkyl-4Oxo-1-phenyl-4,5,6,7,-tetrahydroindazoles and their oximes in polyphosphoric acid" J. Chem. Soc. Perkin Transactions, vol. 1, No. 22: (1973), pp. 2697-2703.

Nussbaumer, et al., "Synthesis and Structure-Activity Relationships of Side-Chain-Substituted Analogs of the Allylamine Antimycotic Terbinafine Lacking the Central Amino Function,"J. Med. Chem., vol. 38, No. 10 (1995) pp. 1831-1836.

Perner, et al.,"In Vitro Structure-Activity Relationship and In Vivo Characterization of 1-(Aryl)-3-(4-(amino)benzyl) urea Transient Receptor Potential Vanilloid 1 Antagonists," J Med. Chem., vol. 50 (2007), pp. 3651-3660.

Pircio, et al., "A New Method for the Evaluation of Analgesic Activity using Adjuvant-Induced Arthritis in the Rat" Eur J. Pharmacol. vol. 31, No. 2 (1975), pp. 207-215.

Prescott, et al., Methods in Cell Biology, Academic Press, New York, N. Y. vol. 14, No. 33 et seq. (1976).

Prijs, et al. "9. On a few derivatives of heterocyclic carbonic acids I. Metal ions and biological action, 16th report," Helv. Chim. Acta, vol. 37 (1954), pp. 90-94. Translation.

Roe, et al., "The preparation of heterocyclic fluorine compounds by the schiemann reaction. III. Some monofluoroisoquinolines," J. Am. Chem. Soc., vol. 73 (1951), pp. 687-689.

Sato, et al., "Construction of optically pure tryptophans from serine derived aziridine-2-carboxylates," Tetrahedron Letters, vol. 30, No. 31 (1989), pp. 4073-4076.

Sterling, "Novel Dual Inhibitors of AchE and MAO," Journal of Medicinal Chemistry, vol. 45, No. 24 (2002), pp. 5260-5279.

Taurins, et al., "Thiazoloisoquinolines. IV. The synthesis and spectra of thiazolo[4,5-h]-and thiazolo[5,4-f] isoquinolines. The ultraviolet and proton magnetic resonance spectra of some substituted isoquinolines," Canadian Journal of Chemistry, vol. 49, No. 24 (1971), pp. 4054-4061.

Thummel, et al., "Polyaza Cavity-Shaped Molecules. Annelated Derivatives of 2-(2'-Pyridyl)-1,8-naphthyridine and 2,2'-Bi-1,8-naphthyridine" J. Org. Chem., vol. 49 (1984) pp. 2208-2212.

Warpehoski, et al., "Stereoelectronic factors influencing the biological activity and DNA interaction of synthetic antitumor agents modeled on CC-1065," J. Med. Chem., vol. 31 (1988), pp. 590-603.

International Search Report, European Patent Office (Dec. 20, 2007).

Honma, et al., Journal of Med. Chem., 44; 4615-4627 (2001).

Gall, et al., Helv Chim Acta, 38(171):1421-1423 (1955).

Euw, et al., Helv Chim Acta, 37; 90-94 (1954).

Fiesser, et al., J. Amer. Chem. Soc., 57:1840-1844 (1935).

Taurins, et al., Canadian Journal of Chemistry 49(24): 4054-4061 (1971).

Mooney, et al., J. Med. Chem., 17(11): 1145-1150 (1974).

Craig, et al., J. Amer. Chem. Soc., 64-783-784 (1942).

Naruto, et al., Chemical and Pharm. Bulletin 20(10):2163-2171 (1972).

Cannon, et al., J. Heterocycle Chem., 19:1195-1199 (1982).

Kumar, et al., Indian Journal of Chem., 31:177-182 (1992).

Journal of Med. Chem., 36:1104-1107 (1993).

* cited by examiner

COMPOUNDS THAT INHIBIT TRPV1 AND USES THEREOF

RELATED APPLICATION

This application claims priority to U.S. Patent Application Ser. No. 60/840,254, filed Aug. 25, 2006 and is incorporated herein by reference in its entirety.

TECHNICAL FIELD

The present invention relates to compounds of formula (I) which are TRPV1 antagonists and are useful for treating disease or disorder such as pain, neuropathic pain, allodynia, pain associated with inflammation or an inflammatory disease, inflammatory hyperalgesia, bladder overactivity, or urinary incontinence. Pharmaceutical compositions comprising compounds of formula (I) and methods for treating pain, neuropathic pain, allodynia, pain associated with inflammation or an inflammatory disease, inflammatory hyperalgesia, bladder overactivity, or urinary incontinence are also included.

BACKGROUND OF INVENTION

Nociceptors are primary sensory afferent (C and Aδ fibers) neurons that are activated by a wide variety of noxious stimuli including chemical, mechanical, thermal, and proton (pH <6) modalities. The lipophillic vanilloid, capsaicin, activates primary sensory fibers via a specific cell surface capsaicin receptor, cloned as the transient receptor potential vanilloid-1 (TRPV1). The intradermal administration of capsaicin is characterized by an initial burning or hot sensation followed by a prolonged period of analgesia. The analgesic component of TRPV1 receptor activation is thought to be mediated by a capsaicin-induced desensitization of the primary sensory afferent terminal. Thus, the long lasting anti-nociceptive effect of capsaicin has prompted the clinical use of capsaicin analogs as analgesic agents. Further, capsazepine, a capsaicin receptor antagonist, can reduce inflammation-induced hyperalgesia in animal models. TRPV1 receptors are also localized on sensory afferents which innervate the bladder. Capsaicin or resiniferatoxin has been shown to ameliorate incontinence symptoms upon injection into the bladder.

The TRPV 1 receptor has been called a "polymodal detector" of noxious stimuli since it can be activated in several ways. The receptor channel is activated by capsaicin and other vanilloids and thus is classified as a ligand-gated ion channel. TRPV1 receptor activation by capsaicin can be blocked by the competitive TRPV1 receptor antagonist, capsazepine. The channel can also be activated by protons. Under mildly acidic conditions (pH 6-7), the affinity of capsaicin for the receptor is increased, whereas at pH<6, direct activation of the channel occurs. In addition, when membrane temperature reaches 43° C., the channel is opened. Thus heat can directly gate the channel in the absence of ligand. The capsaicin analog, capsazepine, which is a competitive antagonist of capsaicin, blocks activation of the channel in response to capsaicin, acid, or heat.

The channel is a nonspecific cation conductor. Both extracellular sodium and calcium enter through the channel pore, resulting in cell membrane depolarization. This depolarization increases neuronal excitability, leading to action potential firing and transmission of a noxious nerve impulse to the spinal cord. In addition, depolarization of the peripheral terminal can lead to release of inflammatory peptides such as, but not limited to, substance P and CGRP, leading to enhanced peripheral sensitization of tissue.

Recently, two groups have reported the generation of a "knock-out" mouse lacking the TRPV1 receptor. Electrophysiological studies of sensory neurons (dorsal root ganglia) from these animals revealed a marked absence of responses evoked by noxious stimuli including capsaicin, heat, and reduced pH. These animals did not display any overt signs of behavioral impairment and showed no differences in responses to acute non-noxious thermal and mechanical stimulation relative to wild-type mice. The TRPV1 (−/−) mice also did not show reduced sensitivity to nerve injury-induced mechanical or thermal nociception. However, the TRPV1 knock-out mice were insensitive to the noxious effects of intradermal capsaicin, exposure to intense heat (50-55° C.), and failed to develop thermal hyperalgesia following the intradermal administration of carrageenan.

Further, as known in the art, cytochrome P450 enzymes are heme-containing membrane proteins localized in the smooth endoplasmic reticulum of numerous tissues, including, in particular, the liver. This family of enzymes catalyzes a wide variety of oxidative and reductive reactions and has activity towards a chemically diverse group of substrates. These enzymes are the major catalysts of drug biotransformation reactions and also serve an important detoxification role in the body. CYP3A is both the most abundant and most clinically significant subfamily of cytochrome P450 enzymes. The CYP3A subfamily has four human isoforms, 3A4, 3A5, 3A7 and 3A43, with CYP3A4 being the most commonly associated with drug interactions. The CYP3A isoforms make up approximately 50% of the liver's total cytochrome P450 and are widely expressed throughout the gastrointestinal tract, kidneys and lungs and therefore are ultimately responsible for the majority of first-pass metabolism of drugs and toxins, leading to their disposition from the body. This is important as increases or decreases in first-pass metabolism can have the effect of administering a much smaller or larger dose of drug than usual. Inhibition of these enzymes can possibly lead to life-threatening conditions where the enzyme is not able to perform this function. More than 150 drugs are known substrates of CYP3A4, including many of the opiate analgesics, steroids, antiarrhythmic agents, tricyclic antidepressants, calcium-channel blockers and macrolide antibiotics.

Certain VR1 antagonists are discussed in U.S. Pat. No. 6,933,311. However, interactions with CYP3A4 for these compounds are unknown.

Accordingly, the need exists to develop TRPV1 antagonists that exhibit low inhibitory activity against drug metabolism enzyme CYP3A4. Such antagonists should possess a much lower risk of drug-drug interactions with CYP3A4 in human drug metabolism and serve well as safe pharmaceutical agents with fewer limitations on therapies involving combinations of drugs. Such compounds should also provide beneficial pharmaceutical characteristics while minimizing undesirable side effects generally associated with inhibition of cytochrome P450 enzymes.

SUMMARY

The present invention relates to compounds of formula (I) or a pharmaceutically acceptable salt thereof,

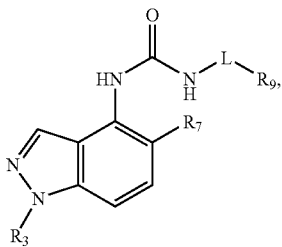

(I)

wherein

L is $C_1$-$C_5$ alkylene;

$R_3$ is $C_1$-$C_5$ alkyl;

$R_7$ is selected from the group consisting of hydrogen and halogen; and $R_9$ is aryl;

with the proviso that the following compounds are excluded:

N-(4-chlorobenzyl)-N'-(1-methyl-1H-indazol-4-yl)urea,

N-(4-tert-butylbenzyl)-N'-(1-methyl-1H-indazol-4-yl) urea,

N-(3-fluoro-4-(trifluoromethyl)benzyl)-N'-(1-methyl-1H-indazol-4-yl)urea,

N-(4-fluoro-3-(trifluoromethyl)benzyl)-N'-(1-methyl-1H-indazol-4-yl)urea,

N-(3,4-dichlorobenzyl)-N'-(1-methyl-1H-indazol-4-yl) urea,

N-(2,4-dichlorobenzyl)-N'-(1-methyl-1H-indazol-4-yl) urea,

N-(4-ethylbenzyl)-N'-(1-methyl-1H-indazol-4-yl)urea,

N-(2-chlorobenzyl)-N'-(1-methyl-1H-indazol-4-yl)urea,

N-(4-fluorobenzyl)-N'-(1-methyl-1H-indazol-4-yl)urea,

N-(2-fluorobenzyl)-N'-(1-methyl-1H-indazol-4-yl)urea,

N-[1-(4-bromophenyl)ethyl-N'-(1-methyl-1H-indazol-4-yl)urea, and

N-(1-methyl-1H-indazol-4-yl)-N'-{4-[(trifluoromethyl) thio]benzyl}urea.

The inventions further relates to a pharmaceutical composition comprising a compound of formula (I) or a pharmaceutically acceptable salt or solvate thereof, and one or more pharmaceutically acceptable carriers, alone or in combination with one or more nonsteroidal anti-inflammatory drug (NSAID).

Included also are methods for treating diseases or disorders as defined herein below, said methods comprises the step of administering a therapeutically effective amount of a compound of formula (I), or a pharmaceutically acceptable salt thereof, to a subject in need thereof, alone or in combination with one or more nonsteroidal anti-inflammatory drug (NSAID).

Yet further, the invention provides the use of a compound of formula (I), or a pharmaceutically acceptable salt thereof, in the manufacture of a medicament for the treatment of disease or disorders as defined herein below, alone or in combination with one or more nonsteroidal anti-inflammatory drug (NSAID).

It is to be understood that both the foregoing general description and the following detailed description are exemplary, but are not restrictive, of the invention.

DETAILED DESCRIPTION OF THE PRESENT INVENTION

Compounds of formula (I) are disclosed in this invention,

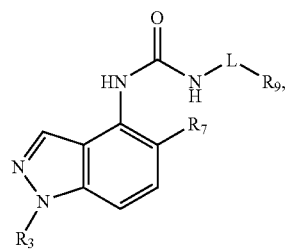

(I)

wherein $R_3$, $R_7$, $R_9$ and L are defined above in the Summary of the Invention and below in the Detailed Description. Preferably, compounds of the invention are TRPV1 antagonists that exhibit low inhibitory activity against CYP3A4. Further, compositions comprising such compounds and methods for treating conditions and disorders using such compounds and compositions are also disclosed.

In various embodiments, the present invention provides at least one variable that occurs more than one time in any substituent or in the compound of the invention or any other formulae herein. Definition of a variable on each occurrence is independent of its definition at another occurrence. Further, combinations of substituents are permissible only if such combinations result in stable compounds. Stable compounds are compounds, which can be isolated from a reaction mixture.

a. Definition

As used in the specification and the appended claims, unless specified to the contrary, the following terms have the meaning indicated:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through an alkoxy group, as defined herein. Representative examples of alkoxyalkoxy include, but are not limited to, methoxymethoxy, ethoxymethoxy and 2-ethoxyethoxy.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 3-methoxycarbonyl-3,3-dimethylpropyl, ethoxycarbonylbutyl, and 2-tert-butoxycarbonylethyl.

The term "alkyl" as used herein, means a straight or branched chain saturated hydrocarbon containing from 1 to 10 carbon atoms, for example, from 1 to 6 carbon atoms. Representative examples of alkyl include, but are not limited to, methyl, ethyl, n-propyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, 3,3-dimethylbutyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylene" means a divalent group derived from a straight or branched chain hydrocarbon of from 1 to 10 carbon atoms. Representative examples of alkylene include, but are not limited to, —$CH_2$—, —$CH_2CH_2$—, —$CH_2CH_2CH_2$—, —$CH_2CH_2CH_2CH_2$—, and —$CH_2CH(CH_3)CH_2$—.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylsulfanyl, ethylsulfanyl, tert-butylsulfanyl, and hexylsulfanyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means a phenyl group, or a bicyclic fused ring system wherein one or more of the rings are phenyl group. Bicyclic fused ring systems are exemplified by a phenyl group fused to a monocyclic cycloalkyl group, a monocyclic cycloalkenyl group, or another phenyl group. Representative examples of aryl include, but are not limited to, indanyl, indenyl, naphthyl, phenyl and tetrahydronaphthyl. The aryl groups of the present invention can be attached to the parent molecular moiety through any substitutable atom within the phenyl group.

The aryl groups of this invention can be substituted with 1, 2, 3, 4 or 5 substituents independently selected from alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, carboxy, carboxyalkyl, cyano, cyanoalkyl, formyl, formylalkyl, haloalkoxy, haloalkyl, haloalkylthio, halogen, hydroxy, hydroxyalkyl, methylenedioxy, mercapto, mercaptoalkyl, nitro, —$NZ_CZ_D$, ($NZ_CZ_D$)alkyl, ($NZ_CZ_D$)carbonyl, ($NZ_CZ_D$)carbonylalkyl, ($NZ_CZ_D$)sulfonyl, —$NR_AS(O)_2R_B$, —$S(O)_2OR_A$ and —$S(O)_2R_A$ wherein $R_A$ and $R_B$ are each independently selected from the group consisting of hydrogen and alkyl. Representative examples of substituted aryl include, but are not limited to, 2-(3,3-dimethylbutyl)-4-(trifluoromethyl)phenyl, 2-isobutyl-4-(trifluoromethyl)phenyl, 2-isopropyl-4-(trifluoromethyl)phenyl, methyl 2,2-dimethyl-4-(4-(trifluoromethyl)phenyl)butanoate, 2,2-dimethyl-4-(4-(trifluoromethyl)phenyl)butanoic acid, 2-(4-hydroxy-3,3-dimethylbutyl)-4-(trifluoromethyl)phenyl, 4-chloro-3-(3,3,-dimethylbutyl)phenyl, and 4-chloro-3-isopropylphenyl.

The term "carbonyl" as used herein, means a —C(O)— group.

The term "carboxy" as used herein, means a —$CO_2H$ group.

The term "carboxyalkyl" as used herein, means a carboxy group, as defined herein, appended to the parent molecular moiety through an alkyl group, as defined herein. Representative examples of carboxyalkyl include, but are not limited to, carboxymethyl, 2-carboxyethyl, 3-carboxy-3,3-dimethylpropyl, and 3-carboxypropyl.

The term "cyano" as used herein, means a —CN group.

The term "cyanoalkyl" as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "monocyclic cycloalkenyl" as used herein, means a monocyclic hydrocarbon ring system containing three, four, five, six-, seven or eight carbon atoms and zero heteroatoms in the ring. The three or four-membered ring systems have one double bond, the five- or six-membered ring systems have one or two double bonds, and the seven- or eight-membered ring systems have one, two or three double bonds. Representative examples of monocyclic ring systems include, but are not limited to, cyclohexenyl and cyclopentenyl.

The term "monocyclic cycloalkyl" as used herein, means a saturated monocyclic hydrocarbon ring containing from 3 to 8 carbon atoms and zero heteroatom in the ring. Examples of monocyclic ring systems include cyclopropyl, cyclobutyl, cyclopentyl, cyclohexyl, cycloheptyl, and cyclooctyl.

The term "formyl" as used herein, means a —C(O)H group.

The term "formylalkyl" as used herein, means a formyl group, as defined herein, appended to the parent molecular moiety through an alkyl group, as defined herein. Representative examples of formylalkyl include, but are not limited to, formylmethyl and 2-formylethyl.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, 2-chloro-3-fluoropentyloxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "haloalkylthio" as used herein, means at least one halogen, as defined herein, appended to the parent molecular moiety through an alkylthio group, as defined herein. Representative examples of haloalkylthio include, but are not limited to, trifluoromethylthio.

The term "hydroxy" as used herein, means an —OH group.

The term "hydroxyalkyl" as used herein, means at least one hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, 4-hydroxy-3,3-dimethylbutyl, and 2-ethyl-4-hydroxyheptyl.

The term "mercapto" as used herein, means a —SH group.

The term "mercaptoalkyl" as used herein, means a mercapto group, as defined herein, appended to the parent molecular moiety through an alkyl group, as defined herein. Representative examples of mercaptoalkyl include, but are not limited to, 2-mercaptoethyl and 3-mercaptopropyl.

The term "nitro" as used herein, means a —NO$_2$ group.

The term "—NZ$_C$Z$_D$" as used herein, means two groups, Z$_C$ and Z$_D$, which are appended to the parent molecular moiety through a nitrogen atom. Z$_C$ and Z$_D$ are each independently selected from hydrogen, alkyl, alkylcarbonyl, and formyl. Representative examples of —NZ$_C$Z$_D$ include, but are not limited to, amino, methylamino, acetylamino, and acetylmethylamino.

The term "(NZ$_C$Z$_D$)alkyl" as used herein, means a —NZ$_C$Z$_D$ group, as defined herein, appended to the parent molecular moiety through an alkyl group, as defined herein. Representative examples of (NZ$_C$Z$_D$)alkyl include, but are not limited to, aminomethyl, 2-(methylamino)ethyl, 2-(dimethylamino)ethyl and (ethylmethylamino)methyl.

The term "(NZ$_C$Z$_D$)carbonyl" as used herein, means a —NZ$_C$Z$_D$ group, as defined herein, appended to the parent molecular moiety through a carbonyl group, as defined herein. Representative examples of (NZ$_C$Z$_D$)carbonyl include, but are not limited to, aminocarbonyl, (methylamino)carbonyl, (dimethylamino)carbonyl and (ethylmethylamino)carbonyl.

The term "(NZ$_C$Z$_D$)carbonylalkyl" as used herein, means a (NZ$_C$Z$_D$)carbonyl group, as defined herein, appended to the parent molecular moiety through an alkyl group, as defined herein. Representative examples of (NZ$_C$Z$_D$)carbonylalkyl include, but are not limited to, (aminocarbonyl)methyl, 2-((methylamino)carbonyl)ethyl and ((dimethylamino)carbonyl)methyl.

The term "(NZ$_C$Z$_D$)sulfonyl" as used herein, means a —NZ$_C$Z$_D$ group, as defined herein, appended to the parent molecular moiety through a sulfonyl group, as defined herein. Representative examples of (NZ$_C$Z$_D$)sulfonyl include, but are not limited to, aminosulfonyl, (methylamino)sulfonyl, (dimethylamino)sulfonyl and (ethylmethylamino)sulfonyl.

The term "oxo" as used herein, means =O.

The term "sulfonyl" as used herein, means a —S(O)$_2$— group.

b. Compounds

Compounds of the invention have the general formula (I) as described above.

Particular values of variable groups in compounds of formula (I) are as follows. Such values may be used where appropriate with any of the other values, definitions, claims or embodiments defined hereinbefore or hereinafter.

Embodiments of the present invention include compounds of formula (I) wherein R$_9$ is selected form the group consisting of indanyl, indenyl, naphthyl, phenyl and tetrahydronaphthyl, each of which is optionally substituted as disclosed in the Definition. Particularly, R$_9$ is phenyl. More particularly, R$_9$ is substituted phenyl. Another embodiment is directed to compounds of formula (I) wherein L is —CH$_2$—. A further embodiment is directed to compounds of formula (I) wherein R$_3$ is methyl. Examples of compounds of formula (I) include those wherein R$_7$ is hydrogen; R$_3$ is methyl; L is —CH$_2$—, and R$_9$ is phenyl. Yet other examples of compounds of the present invention include compounds of formula (I) wherein R$_7$ is fluorine; R$_3$ is methyl; L is —CH$_2$—, and R$_9$ is phenyl. It is understood that when R$_9$ is phenyl, phenyl can be optionally substituted with 1, 2, 3, 4 or 5 substituents as described herein above. Particularly, phenyl is substituted with two substituents selected from the group consisting of alkyl, halogen, haloalkyl, hydroxyalkyl, carboxyalkyl, and alkoxycarbonylalkyl. Preferably, the phenyl group is substituted with two substituents selected from the group consisting of alkyl (for example, isobutyl, isopropyl, 3,3-dimethylbutyl), halogen (e.g. Cl) and haloalkyl (e.g. trifluoromethyl).

Exemplary compounds of the present invention include, but are not limited to, 1-(2-(3,3-dimethylbutyl)-4-(trifluoromethyl)benzyl)-3-(1-methyl-1H-indazol-4-yl)urea; methyl 2,2-dimethyl-4-(2-((3-(1-methyl-1H-indazol-4-yl)ureido)methyl)-5-(trifluoromethyl)phenyl)butanoate; 1-(2-(4-hydroxy-3,3-dimethylbutyl)-4-(trifluoromethyl)benzyl)-3-(1-methyl-1H-indazol-4-yl)urea; 2,2-dimethyl-4-(2-((3-(1-methyl-1H-indazol-4-yl)ureido)methyl)-5-trifluoromethyl)phenyl)butanoic acid; 1-[4-Chloro-3-(3,3-dimethylbutyl)benzyl]-3-(1-methyl-1H-indazol-4-yl)urea; 1-(2-isobutyl-4-(trifluoromethyl)benzyl)-3-(1-methyl-1H-indazol-4-yl)urea; 1-(2-isopropyl-4-(trifluoromethyl)benzyl)-3-(1-methyl-1H-indazol-4-yl)urea; and 1-(4-Chloro-3-isopropylbenzyl)-3-(1-methyl-1H-indazol-4-yl)urea.

Another embodiment of the present invention is a pharmaceutical composition comprising a therapeutically effective amount of a compound of formula (I), particularly 1-(2-(3,3-dimethylbutyl)-4-(trifluoromethyl)benzyl)-3-(1-methyl-1H-indazol-4-yl)urea, or a pharmaceutically acceptable salt thereof, and one or more pharmaceutically acceptable carriers, alone or in combination with a one or more nonsteroidal anti-inflammatory drug (NSAID).

c. Biological Data (i) In Vitro Data—Determination of Inhibition Potencies

Dulbecco's modified Eagle medium (D-MEM)(with 4.5 mg/mL glucose) and fetal bovine serum were obtained from Hyclone Laboratories, Inc. (Logan, Utah). Dulbecco's phosphate-buffered saline (D-PBS)(with 1 mg/mL glucose and 3.6 mg/l Na pyruvate) (without phenol red), L-glutamine, hygromycin B, and Lipofectamine™ were obtained from Life Technologies (Grand Island, N.Y.). G418 sulfate was obtained from Calbiochem-Novabiochem Corp. (San Diego, Calif.). Capsaicin (8-methyl-N-vanillyl-6-nonenamide) was obtained from Sigma-Aldrich, Co. (St. Louis, Mo.). Fluo-4 AM (N-[4-[6-[(acetyloxy)methoxy]-2,7-difluoro-3-oxo-3H-xanthen-9-yl]-2-[2-[2-[bis [2-[(acetyloxy)methoxy]-2-oxyethyl]amino]-5-methylphenoxy]ethoxy]phenyl]-N-[2-

[(acetyloxy)methoxy]-2-oxyethyl]-glycine, (acetyloxy) methyl ester) was purchased from Molecular Probes (Eugene, Oreg.).

The cDNAs for the human TRPV1 receptor were isolated by reverse transcriptase-polymerase chain reaction (RT-PCR) from human small intestine poly A+RNA supplied by Clontech (Palo Alto, Calif.) using primers designed surrounding the initiation and termination codons identical to the published sequences (Hayes et al. Pain 88: 205-215, 2000). The resulting cDNA PCR products were subcloned into pCIneo mammalian expression vector (Promega) and fully sequenced using fluorescent dye-terminator reagents (Prism, Perkin-Elmer Applied Biosystems Division) and a Perkin-Elmer Applied Biosystems Model 373 DNA sequencer or Model 310 genetic analyzer. Expression plasmids encoding the hTRPV1 cDNA were transfected individually into 1321N1 human astrocytoma cells using Lipofectamine™. Forty-eight hours after transfection, the neomycin-resistant cells were selected with growth medium containing 800 µg/mL Geneticin (Gibco BRL). Surviving individual colonies were isolated and screened for TRPV1 receptor activity. Cells expressing recombinant homomeric TRPV1 receptors were maintained at 37° C. in D-MEM containing 4 mM L-glutamine, 300 µg/mL G418 (Cal-biochem) and 10% fetal bovine serum under a humidified 5% $CO_2$ atmosphere.

The functional activity of compounds at the TRPV1 receptor was determined with a $Ca^{2+}$ influx assay and measurement of intracellular $Ca^{2+}$ levels ($[Ca^{2+}]_i$). All compounds were tested over an 11-point half-log concentration range. Compound solutions were prepared in D-PBS (4× final concentration), and diluted serially across 96-well v-bottom tissue culture plates using a Biomek 2000 robotic automation workstation (Beckman-Coulter, Inc., Fullerton, Calif.). A 0.2 µM solution of the TRPV1 agonist capsaicin was also prepared in D-PBS. The fluorescent $Ca^{2+}$ chelating dye fluo-4 was used as an indicator of the relative levels of $[Ca^{2+}]_i$ in a 96-well format using a Fluorescence Imaging Plate Reader (FLIPR)(Molecular Devices, Sunnyvale, Calif.). Cells were grown to confluency in 96-well black-walled tissue culture plates. Then, prior to the assay, the cells were loaded with 100 µL per well of fluo-4 AM (2 µM, in D-PBS) for 1-2 hours at 23° C. Washing of the cells was performed to remove extracellular fluo-4 AM (2×1 mL D-PBS per well), and afterward, the cells were placed in the reading chamber of the FLIPR instrument. 50 µL of the compound solutions were added to the cells at the 10 second time mark of the experimental run. Then, after a 3 minute time delay, 50 µL of the capsaicin solution was added at the 190 second time mark (0.05 µM final concentration) (final volume=200 µL) to challenge the TRPV1 receptor. Time length of the experimental run was 240 seconds. Fluorescence readings were made at 1 to 5 second intervals over the course of the experimental run. The peak increase in relative fluorescence units (minus baseline) was calculated from the 190 second time mark to the end of the experimental run, and expressed as a percentage of the 0.05 µM capsaicin (control) response. Curve-fits of the data were solved using a four-parameter logistic Hill equation in GraphPad Prism® (GraphPad Software, Inc., San Diego, Calif.), and $IC_{50}$ values were calculated.

The compounds of the present invention were found to be antagonists of the transient receptor potential vanilloid-1 (TRPV 1) receptor with $IC_{50s}$ from 1000 nM to 0.1 nM. In a preferred range, compounds tested had $IC_{50s}$ from 500 nM to 0.1 nM. In a more preferred range, compounds tested had $IC_{50s}$ from 50 nM to 0.1 nM.

(ii) In Vivo Data—Determination of Antinociceptive Effect

Experiments were performed on 400 adult male 129J mice (Jackson laboratories, Bar Harbor, Me.), weighing 20-25 g. Mice were kept in a vivarium, maintained at 22° C., with a 12 hour alternating light-dark cycle with food and water available ad libitum. All experiments were performed during the light cycle. Animals were randomly divided into separate groups of 10 mice each. Each animal was used in one experiment only and was sacrificed immediately following the completion of the experiment. All animal handling and experimental procedures were approved by an IACUC Committee.

The antinociceptive test used was a modification of the abdominal constriction assay described in Collier, et al., Br. J. Pharmacol. Chemother. 32 (1968) 295-310. Each animal received an intraperitoneal (i.p.) injection of 0.3 mL of 0.6% acetic acid in normal saline to evoke writhing. Animals were placed separately under clear cylinders for the observation and quantification of abdominal constriction. Abdominal constriction was defined as a mild constriction and elongation passing caudally along the abdominal wall, accompanied by a slight twisting of the trunk and followed by bilateral extension of the hind limbs. The total number of abdominal constrictions was recorded from 5 to 20 minutes after acetic acid injection. The $ED_{50s}$ were determined based on the i.p. injection.

The compounds of the present invention tested were found to have antinociceptive effects with $ED_{50s}$ from 1 mg/kg to 500 mg/kg. The in vitro and in vivo data demonstrates that compounds of the present invention antagonize the TRPV 1 receptor and are useful for treating disorders caused by or exacerbated by TRPV1 receptor activity.

(iii) In Vitro Data—CYP3A Inhibition

The potential time dependent inhibitory effect of these compounds on the activity of human CYP3A was evaluated in vitro in human liver microsomes. The activity of the CYP3A4 was indirectly determined by measuring the conversion of midazolam to the metabolite 1'-hydroxy-midazolam.

A typical experiment included human liver microsomes (0.1 mg/mL protein) (BD Gentest from BDbioscience, BD Biosciences, San Jose, Calif.) in potassium phosphate buffer (50 mM, pH 7.4) and any of the compounds of the present invention in different increasing concentrations.

1 µM, 3 µM, and 10 µM of representative compounds of the present invention were mixed with human liver microsomes (0.1 mg/mL protein) in potassium phosphate buffer (50 mM, pH 7.4). The mixtures were pre-warmed for 5 minutes at 37° C. in a water bath and the pre-incubation initiated with the addition of NADPH (1 mM). Following a 15-minute pre-incubation, midazolam (2 µM) was added, and the incubation was allowed to continue for an additional 5 minutes. The reaction was terminated by the addition of a (50/50, v/v) mixture of methanol and acetonitrile (containing an internal standard), equal to half of the incubation volume. Following centrifugation, the supernatant was used for LC-MS-MS determination of inhibition of the conversion of midazolam to the metabolite 1'-hydroxy-midazolam under the assay conditions.

The compounds of the invention were tested in the inhibition of CYP3A4 assay as described above. The $IC_{50}$ values are presented in Table 1.

TABLE 1

|  | Example 1 | Example 4 | Example 2 | Example 3 | Example 5 |
|---|---|---|---|---|---|
| CYP 3A IC$_{50}$(μM) | <1 | <1 | >30 | >30 | >30 |

Compounds of the invention inhibit CYP3A4 with IC$_{50}$ greater than 30 μM, for example, 30-50 μM.

The data in Table 1 demonstrates that compounds of the present invention have little or no effect on drug metabolizing enzymes, such as CYP3A4. This interesting property may results in better dosage quantities of the TRPV1 anatagonists, with which the same beneficial therapeutic effects can be induced without or at least with minimized undesirable side effects generally associated with the inhibition of cytochrome P450 enzymes.

d. Methods of Using the Compounds

One embodiment of the present invention provides a method for treating a disorder that may be ameliorated by inhibiting vanilloid receptor subtype 1 (TRPV1) receptor in a host mammal in need of such treatment. The method comprises administering a therapeutically effective amount of a compound of formula (I) or a pharmaceutically acceptable salt thereof. Preferably, the compound is 1-(2-(3,3-dimethylbutyl)-4-(trifluoromethyl)benzyl)-3-(1-methyl-1H-indazol-4-yl)urea.

Another embodiment of the present invention provides a method for treating pain in a mammal in need of such treatment. This method comprises administering a therapeutically effective amount of a compound of formula (I) according to claim 1 or a pharmaceutically acceptable salt thereof. Also, in this method, the compound is 1-(2-(3,3-dimethylbutyl)-4-(trifluoromethyl)benzyl)-3-(1-methyl-1H-indazol-4-yl)urea.

Yet another embodiment of the present invention provides a method of treating ischemia including acute cerebral ischemia, pain including chronic pain, neuropathic pain, nociceptive pain, allodynia, inflammatory pain, inflammatory hyperalgesia, post herpetic neuralgia, neuropathies, neuralgia, diabetic neuropathy, HIV-related neuropathy, nerve injury, rheumatoid arthritic pain, osteoarthritic pain, burns, back pain, visceral pain, cancer pain, dental pain, headache, migraine, carpal tunnel syndrome, fibromyalgia, neuritis, sciatica, pelvic hypersensitivity, pelvic pain, menstrual pain, bladder disease, such as incontinence and bladder overactivity, micturition disorder, renal colic; and cystitis; inflammation such as burns, rheumatoid arthritis and osteoarthritis; neurodegenerative disease such as stroke, post stroke pain and multiple sclerosis; pulmonary disease such as asthma, cough, chronic obstructive pulmonary disease (COPD) and broncho constriction; gastrointestinal disease such as gastroesophageal reflux disease (GERD), dysphagia, ulcer, irritable bowel syndrome (IBS), inflammatory bowel disease (IBD), colitis and Crohn's disease; ischemia such as cerebrovascular ischemia; emesis such as cancer chemotherapy-induced emesis, and obesity, in mammals, especially humans. For example, the compounds of the invention are useful for the treatment of pain, particularly neuropathic pain. This method comprises the step of administering a therapeutically effective amount of a compound of formula (I) or a pharmaceutically acceptable salt thereof, to a subject in need thereof.

Compounds of the present invention, including but not limited to those specified in the examples, can be used to treat pain as demonstrated by Nolano, M. et al., Pain 81 (1999) 135; Caterina, M. J. and Julius, D., Annu. Rev. Neurosci. 24, (2001) 487-517; Caterina, M. J. et al., Science 288 (2000) 306-313; Caterina, M. J. et al., Nature 389 (1997) 816-824.

Compounds of the present invention, including but not limited to those specified in the examples, can be used to treat bladder overactivity and/or urinary incontinence as demonstrated by Fowler, C. Urology 55 (2000) 60.

Compounds of the present invention, including but not limited to those specified in the examples, can be used to treat inflammatory thermal hyperalgesia as demonstrated by Davis, J. et al., Nature 405 (2000) 183-187.

Compounds of the invention may be administered alone, or in combination with one or more other compounds of the invention, or in combination (i.e. co-administered) with one or more additional pharmaceutical agents. For example, a compound of formula (I) or a pharmaceutically acceptable salt or solvate thereof, may be administered in combination with one or more nonsteroidal anti-inflammatory drug (NSAID) such as, but not limited to, aspirin, acetaminophen, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. Combination therapy includes administration of a single pharmaceutical dosage formulation containing one or more of the compounds of invention and one or more additional pharmaceutical agents, as well as administration of the compounds of the invention and each additional pharmaceutical agent, in its own separate pharmaceutical dosage formulation. For example, a compound of formula (I) and one or more additional pharmaceutical agents, may be administered to the patient together, in a single oral dosage composition having a fixed ratio of each active ingredient, such as a tablet or capsule; or each agent may be administered in separate oral dosage formulations.

Where separate dosage formulations are used, compounds of the invention and one or more additional pharmaceutical agents may be administered at essentially the same time (e.g., concurrently) or at separately staggered times (e.g., sequentially).

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

Compounds of the invention can also be administered as a pharmaceutical composition comprising the compounds of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal range from about 0.10 µg/kg body weight to about 10 mg/kg body weight. More preferable doses can be in the range of from about 0.10 µg/kg body weight to about 1 mg/kg body weight. If desired, the effective daily dose can be divided into multiple doses for purposes of administration. Consequently, single dose compositions may contain such amounts or submultiples thereof to make up the daily dose.

e. Pharmaceutical Compositions

The present invention further provides pharmaceutical compositions that comprise compounds of the present invention or a pharmaceutically acceptable salt or solvate thereof. The pharmaceutical compositions comprise compounds of the present invention that may be formulated together with one or more non-toxic pharmaceutically acceptable carriers.

Another aspect of the present invention is a pharmaceutical composition comprising a compound of formula (I), or a pharmaceutically acceptable salt thereof, and one or more pharmaceutically acceptable carriers, alone or in combination with a one or more nonsteroidal anti-inflammatory drug (NSAID).

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

The compounds of the present invention can be used in the form of pharmaceutically acceptable salts derived from inorganic or organic acids. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts are well-known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use.

The present invention contemplates compounds of formula (I) formed by synthetic means or formed by in vivo biotransformation of a prodrug.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

f. General Synthesis

This invention is intended to encompass compounds of the invention when prepared by synthetic processes or by metabolic processes. Preparation of the compounds of the invention by metabolic processes include those occurring in the human or animal body (in vivo) or processes occurring in vitro.

The synthesis of compounds of formula (I) wherein the groups L, $R_3$, $R_7$, and $R_9$ have the meanings as set forth in the summary section unless otherwise noted, is exemplified in the accompanying Schemes 1-6.

As used in the descriptions of the schemes and the examples, certain abbreviations are intended to have the following meanings: dba for dibenzylideneacetone; BINAP for 2,2'-bis(diphenylphosphino)-1,1'-binaphthyl; DIEA for diisopropylethylamine; DMF for N,N-dimethylformamide; DMSO for dimethylsulfoxide; HPLC for high performance liquid chromatography; Pd for palladium; Ph for phenyl; and THF for tetrahydrofuran.

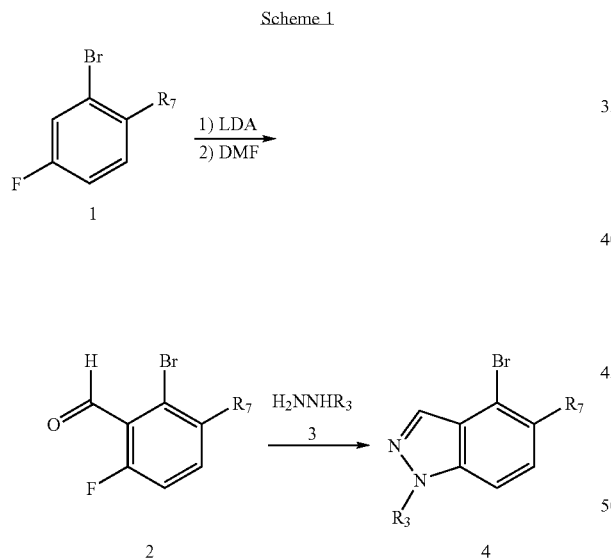

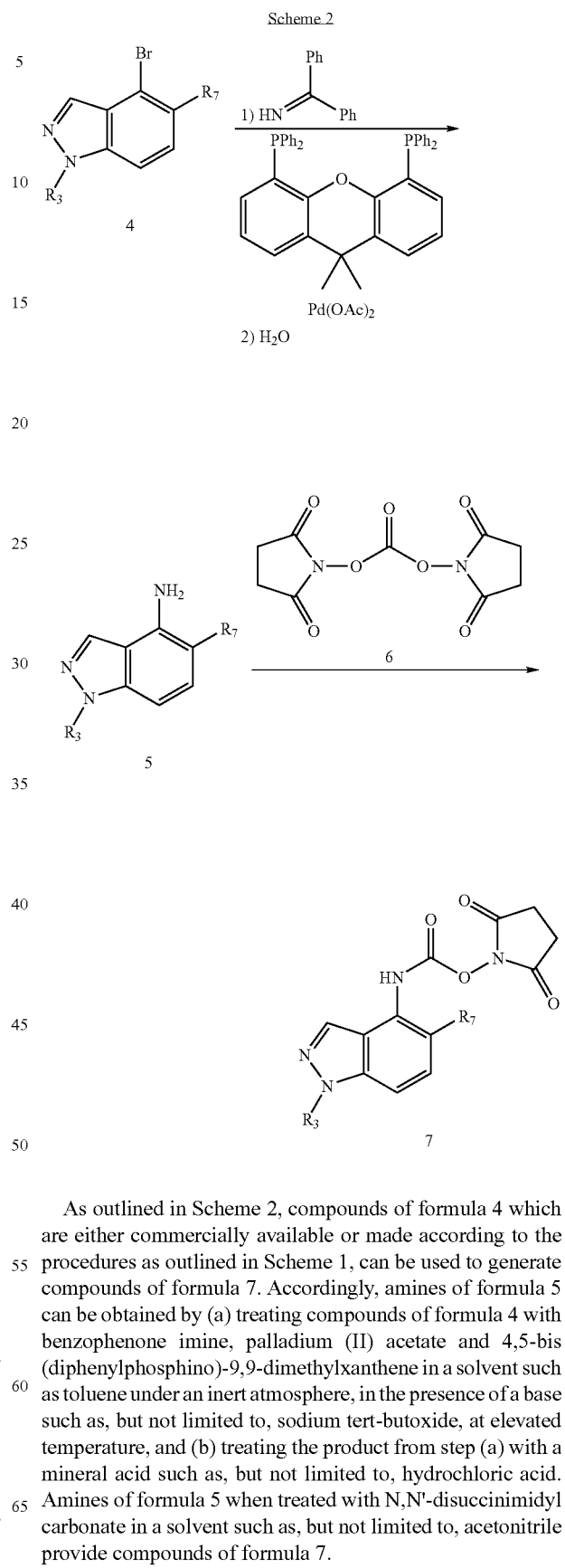

Indazoles of formula 4 can be prepared from substituted phenyls of formula 1 as shown in Scheme 1. Compounds of formula 1, upon treatment with lithium diisopropylamide in a solvent such as tetrahydrofuran at a temperature between about −55° C. to about −78° C., followed by treatment with DMF (or other formyl equivalents known to one skilled in the art) provide compounds of formula 2. Compounds of formula 2 when heated in the presence of hydrazine compounds of formula 3, provide compounds of formula 4.

As outlined in Scheme 2, compounds of formula 4 which are either commercially available or made according to the procedures as outlined in Scheme 1, can be used to generate compounds of formula 7. Accordingly, amines of formula 5 can be obtained by (a) treating compounds of formula 4 with benzophenone imine, palladium (II) acetate and 4,5-bis (diphenylphosphino)-9,9-dimethylxanthene in a solvent such as toluene under an inert atmosphere, in the presence of a base such as, but not limited to, sodium tert-butoxide, at elevated temperature, and (b) treating the product from step (a) with a mineral acid such as, but not limited to, hydrochloric acid. Amines of formula 5 when treated with N,N'-disuccinimidyl carbonate in a solvent such as, but not limited to, acetonitrile provide compounds of formula 7.

Scheme 3

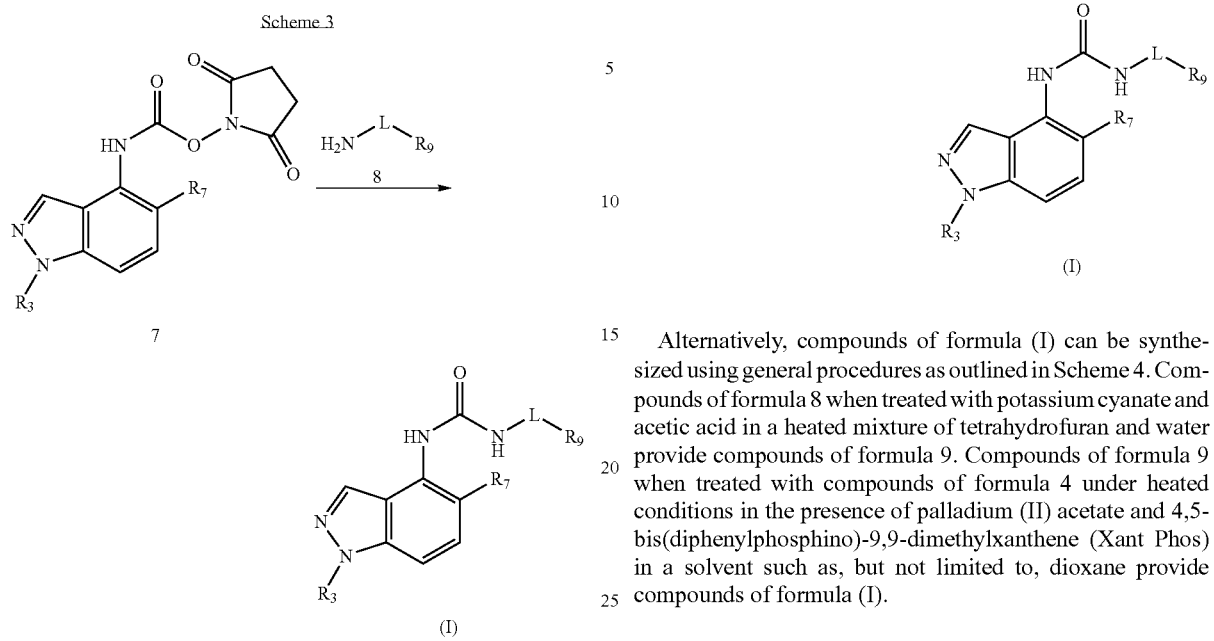

As outlined in Scheme 3, compounds of formula 7 when treated with an amine of formula 8 provide compounds of formula (I). Typical conditions used for this reaction include, but are not limited to, stirring compounds of formula 7 and compounds of formula 8 in the presence or absence of a base such as, but not limited to, diisopropylethylamine in a solvent such as acetonitrile.

Scheme 4

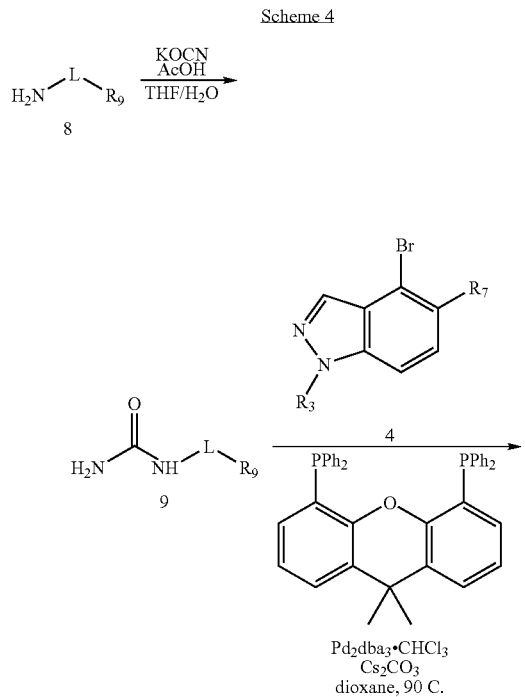

Alternatively, compounds of formula (I) can be synthesized using general procedures as outlined in Scheme 4. Compounds of formula 8 when treated with potassium cyanate and acetic acid in a heated mixture of tetrahydrofuran and water provide compounds of formula 9. Compounds of formula 9 when treated with compounds of formula 4 under heated conditions in the presence of palladium (II) acetate and 4,5-bis(diphenylphosphino)-9,9-dimethylxanthene (Xant Phos) in a solvent such as, but not limited to, dioxane provide compounds of formula (I).

Scheme 5

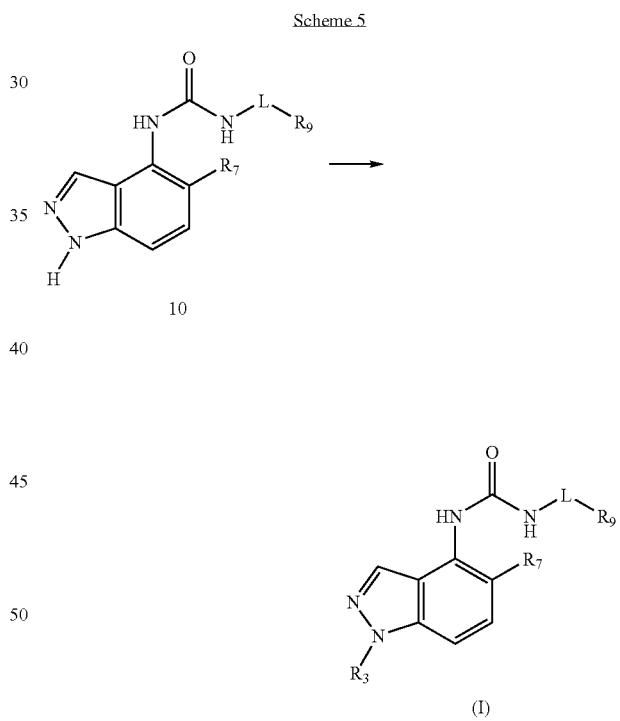

Compounds of formula 10 when treated with a base such as, but not limited to, sodium hydride in a solvent such as DMF, followed by the addition of dimethyl sulfate or methyl iodide provide compounds of formula (I) wherein $R_3$ is methyl. When treated with other alkylating reagents such as $R_3X$ wherein X is halogen after the addition of a base such as sodium hydride, compounds of formula 10 can be converted to compounds of formula (I).

Amines of formula 8 wherein $R_9$ is substituted phenyl, and L is $CH_2$ can be prepared using general procedures as described in Scheme 6.

Scheme 6

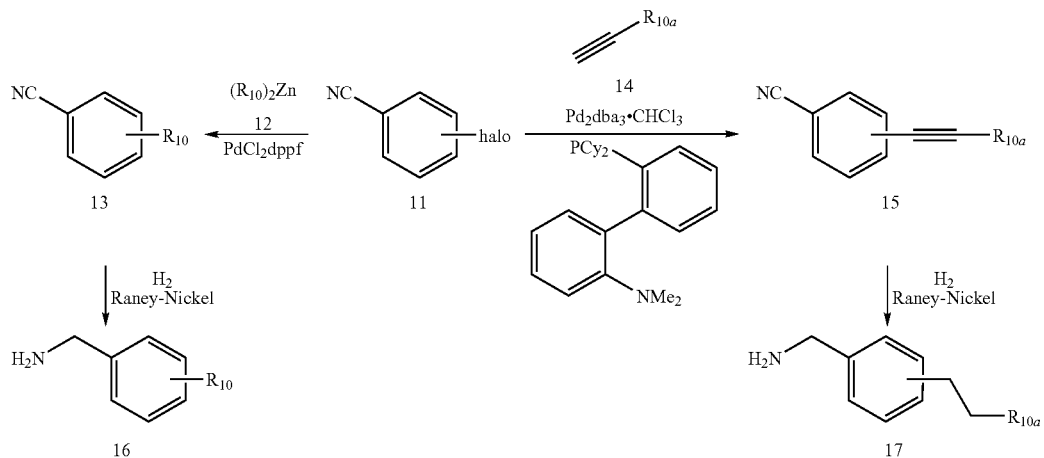

Compounds of formula 11 when treated with compounds of formula 12, wherein $R_{10}$ represents the optional substituents of phenyl moiety in formula (I), in the presence of a palladium catalyst such as, but not limited to, [1,1'-bis(diphenylphosphino)ferrocene]dichloropalladium(II), provide compounds of formula 13. Similarly, compounds of formula 11 can be treated with acetylene containing compounds of formula 14, wherein $R_{10a}$ are alkyl groups in the presence of $Pd_2 dba_3:CHCl_3$ and 2-dicyclohexylphosphino-2'-(N,N-dimethylamino)biphenyl, copper iodide and triethylamine under heated conditions to provide compounds of formula 15. Compounds of formula 13 or 15 when treated with Raney-Nickel in the presence of hydrogen, provide compounds of formula 16 and compounds of formula 17, respectively.

The following Examples are intended as an illustration of and not a limitation upon the scope of the invention as defined in the appended claims.

g. EXAMPLES

Example 1

1-(2-(3,3-dimethylbutyl)-4-(trifluoromethyl)benzyl)-3-(1H-indazol-4-yl)urea

Example 1A 2-(3,3-dimethylbut-1-ynyl)-4-(trifluoromethyl)benzonitrile $Pd_2 dba_3:CHCl_3$ (0.439 g, 0.424 mmol, 1.5%), dicyclohexylphosphino-2'-(N,N-dimethylamino)biphenyl (0.640 g, 1.63 mmol, 6%), and CuI (0.155 g, 0.816 mmol, 3%) were placed in a flask and purged with $N_2$. triethylamine (16 mL) was added and the mixture was stirred for 5 minutes followed by the addition of 3-chloro-4-cyanobenzotrifluoride (4.00 mL, 27.0 mmol) and 3,3-dimethylbutyne (4.00 mmol, 1.2 eq). The mixture was heated under $N_2$ at 65° C. for 2 hours, cooled to ambient temperature and diluted with ethyl acetate (~300 mL). The mixture was washed sequentially with ~2% aqueous $NH_4OH$ (120 mL) and saturated aqueous $NH_4Cl$ (100 mL). The organic layer was dried ($Na_2SO_4$), filtered, concentrated, and filtered through $SiO_2$ (~90 mL) with 4% diethyl ether/Hex to provide the title compound. $^1$H-NMR ($CDCl_3$) δ 7.71-7.75 (m, 2H), 7.58 (dd, 1H), 1.37 (s, 9H).

Example 1B (2-(3,3-dimethylbutyl)-4-(trifluoromethyl)phenyl)methanamine

The product of example 1A was dissolved in 20% $NH_3$/methanol (150 mL), and shaken with RaNi (75 g) under $H_2$ (60 psi) for 16 hours. The mixture was filtered and evaporated under reduced pressure to provide the title compound.

Example 1C 4-(2,5-dioxo-pyrrolidin-1-yloxycarbonylamino)-indazole-1-carboxylic acid methyl ester 4-Amino-indazole-1-carboxylic acid methyl ester (1.9 g, 10 mmol) and disuccinimidylcarbonate (2.8 g, 11 mmol) were mixed in acetonitrile (100 mL) for 48 hours under nitrogen atmosphere. The solid was filtered off, washed with fresh acetonitrile (10 mL) and dried under reduced pressure to provide the title compound.

Example 1D 1-(2-(3,3-dimethylbutyl)-4-(trifluoromethyl)benzyl)-3-(1H-indazol-4-yl)urea To the product of Example 1B dissolved in DMF (80 mL) was added diisopropylethylamine (5.6 mL, 32.1 mmol, 1.2 eq), followed by the addition of the product of Example 1C (8.82 g, 26.5 mmol, 1 eq). The mixture was stirred for 1 hour, diluted with ethyl acetate (600 mL) and the resulting solution washed sequentially with $H_2O$ (1×250 mL) and saturated aqueous $NH_4Cl$ (1×250 mL), dried ($Na_2SO_4$), filtered, and concentrated under reduced pressure. The residue was taken up in 2:1 methanol:THF (90 mL) and 1 N NaOH (30 mL) was added. The solution was stirred 45 minutes, concentrated under reduced pressure to remove the organic solvents. The residue was diluted with ethyl acetate (600 mL), washed sequentially with $H_2O$ (2×200 mL), brine (1×200 mL), dried ($Na_2SO_4$), filtered and concentrated under reduced pressure.

The crude solid was filtered through SiO$_2$ (80 mL) with 4% ethanol in ethyl acetate, stirred over charcoal, filtered and concentrated under reduced pressure, triturated with 4:1 hexane and ethyl ether (150 mL). The solid was recrystallized from methanol and water, filtered and dried under reduced pressure to provide the title compound. $^1$H-NMR (DMSO-d$_6$) δ 12.99 (brs, 1H), 8.79 (brs, 1H), 8.08 (s, 1H), 7.61 (d, 1H), 7.50-7.59 (m, 3H), 7.20 (t, 1H), 7.02 (d, 1H), 6.81 (t, 1H), 4.45 (d, 2H), 2.70 (ddd, 2H), 1.45 (ddd, 2H), 0.97 (s, 9H).

Example 2

1-(2-isobutyl-4-(trifluoromethyl)benzyl)-3-(1-methyl-1H-indazol-4-yl)urea

Example 2A (2-isobutyl-4-(trifluoromethyl)phenyl)methanamine

A solution of 2-methylpropenylmagnesium bromide (0.5 M in THF, 6.0 mL, 3.0 mmol) was added to a solution of ZnCl$_2$ (1.0 M in diethyl ether, 3.0 mL, 3.0 mmol) at 0° C. The mixture was stirred for 10 minutes cold, and an additional 30 min after removing the cooling bath. 2-chloro-4-trifluoromethyl-benzonitrile (0.35 mL, 2.4 mmol) was added, followed by a solution containing Pd$_2$ dba$_3$.CHCl$_3$ (48.5 mg, 0.047 mmol) and 2-dicyclohexylphosphino-2'-(N,N-dimethylamino)biphenyl (56.3 mg, 0.14 mmol) in THF (1 mL). The mixture was stirred at 60° C. for 3 hours, diluted with ethyl acetate and the resulting mixture washed sequentially with 0.1 N aqueous HCl (2×) and brine (1×). The organic layer was dried (Na$_2$SO$_4$), filtered and concentrated under reduced pressure, and purified by flash chromatography (5% diethyl ether/hexane) to provide 0.264 g of the nitrile as a clear oil which was used without further purification. The oil was dissolved in 4:1 methanol:ethyl acetate (25 mL), shaken in the presence of 10% Pd/C and RaNi (catalytic amounts) under H$_2$ (60 psi) overnight. The mixture was filtered and concentrated under reduced pressure, and the residue purified by flash chromatography (20-100% ethyl acetate in dichloromethane as a gradient elution) to provide the title compound. $^1$H NMR (CDCl$_3$) δ 7.43-7.52 (m, 2H), 7.37 (brs, 1H), 3.94 (brs, 2H), 2.57 (d, 2H), 1.87 (m, 1H), 1.49 (brs, 2H), 0.94 (d, 6H).

Example 2B 2-bromo-6-fluorobenzaldehyde

1-Bromo-3-fluorobenzene (17.3 g, 0.1 M) was added over 5 minutes to a solution of lithium diisopropylamide (prepared from the addition of 40 mL of 2.5 N butyllithium in hexanes to 11.5 g of 0.1 M diisopropylamine) in THF at a temperature between −70 and −75° C. The mixture was stirred cold for 1 hour after which DMF (8 mL) was added over 10 minutes. The mixture was stirred cold for an additional 40 minutes followed by the addition of acetic acid (26 g). The mixture was allowed to warm to ambient temperature, transferred into a mixture of 200 mL methyl tert-butyl ether, 200 mL water and 150 mL hydrochloric acid (~4 N). The organic layer was separated and concentrated under reduced pressure to provide the title compound. $^1$H-NMR (CDCl$_3$) δ 10.36 (s, 1H), 7.49 (dt, 1H), 7.40 (dt, 1H), 7.15 (tdd, 1H).

Example 2C 4-bromo-1-methyl-1H-indazole

The product of Example 2B (2.0 g) was dissolved in DMSO (2 g) and the solution was added to methylhydrazine (98%, 3.2 g, 7 eq.). The mixture was heated for 24 hours at 85° C., cooled to ambient temperature and diluted with water (50 mL). The solution was extracted with CH$_2$Cl$_2$ (2×50 mL) and the combined organic layers were dried over MgSO$_4$, filtered and concentrated under reduced pressure to provide the title compound.

Example 2D 1-methyl-1H-indazol-3-amine

A mixture of palladium (II) acetate (82 mg, 2% mol) and xantphos (287 mg, 3% mol) in toluene (10 mL) was stirred for 5 minutes at ambient temperature. To the solution was added a solution of Example 2C (3.68 g, 17.4 mmol) and benzophenone imine (3.0 g, 17.4 mmol) in toluene (30 mL). The mixture was evacuated and purged with nitrogen two times, then stirred at ambient temperature for 15 minutes. sodium tert-butoxide (1.9 g, 1.4 eq) was added and the mixture was evacuated and purged with nitrogen. The mixture was heated to between 80-85° C. for 2 hours, cooled to ambient temperature and diluted with water (30 mL). The aqueous layer was separated and extracted with additional toluene (20 mL). The combined organic layers were stirred with 6 N HCl (10 mL) for 1 hour and 40 mL of water added to dissolve the solids. The toluene layer was discarded and aqueous layer filtered to remove insoluble material. The aqueous layer was adjusted to the pH of 14 with 50% NaOH and filtered to provide the title compound. The solid was dissolved in acetonitrile (25 mL) followed by the slow addition of 12 M HCl to adjust the pH to 1. The precipitate was filtered off, washed with water and dried to provide the hydrochloride salt of the title compound. $^1$H NMR (DMSO) δ 8.03 (d, 1H), 7.02 (dd, 1H), 6.64 (dt, 1H), 6.14 (dd, 1H), 5.73 (brs, 2H), 3.90 (s, 3H).

Example 2E 1-(2-isobutyl-4-(trifluoromethyl)benzyl)-3-(1-methyl-1H-indazol-4-yl)urea A mixture of Example 2D (24 mg, 0.16 mmol) and disuccinimidyl carbonate (38 mg, 0.15 mmol) in acetonitrile (0.4 mL) was stirred at 40° C. for 90 minutes. A solution of Example 2A and diisopropylethylamine (0.028 mL, 0.16 mmol) in DMF (0.4 mL) was added and the mixture stirred for 90 minutes. The solution was diluted with ethyl acetate and extracted with water (2×) and brine (1×). The organic layer was dried (Na$_2$SO$_4$) and concentrated under reduced pressure to provide the title compound. $^1$H NMR (DMSO) δ 8.86 (s, 1H), 8.05 (d, 1H), 7.64 (dd, 1H), 7.54-7.57 (m, 2H), 7.48 (s, 1H), 7.25 (t, 1H), 7.14 (dt, 1H), 6.86 (t, 1H), 4.45 (d, 2H), 3.99 (s, 3H), 2.64 (d, 2H), 1.88 (m, 1H), 0.92 (d, 6H).

Example 3

1-(2-(3,3-dimethylbutyl)-4-(trifluoromethyl)benzyl)-
3-(1-methyl-1H-indazol-4-yl)urea

Example 3A 1-(2-(3,3-dimethylbutyl)-4-(trifluoromethyl)benzyl)
urea

A mixture of Example 1B (9.0 g, 35 mmol), potassium cyanate (4.2 g, 52 mmol), and glacial acetic acid (3.1 mL, 52 mmol) in THF (70 mL) and water (7 mL) was stirred at 60° C. for 2 hours, diluted with ethyl acetate, and sequentially washed with saturated aqueous $NaHCO_3$ and brine. The organic layer was concentrated under reduced pressure to provide the title compound. $^1$H-NMR (DMSO-$d_6$) δ 7.41 (m, 3H), 4.69 (brs, 1H), 4.45 (d, 2H), 4.37 (brs, 2H), 2.64 (ddd, 2H), 1.45 (ddd, 2H), 0.99 (s, 9H).

Example 3B 1-(2-(3,3-dimethylbutyl)-4-(trifluoromethyl)benzyl)-
3-(1-methyl-1H-indazol-4-yl)urea A mixture of Example 3A (5.12 g, 16.9 mmol), Example 2C (3.78 g, 17.9 mmol), $Pd_2$ $dba_3$:$CHCl_3$ (264 mg, 0.255 mmol), xantphos (442 mg, 0.764 mmol), and $Cs_2CO_3$ (8.28 g, 25.4 mmol) in dioxane (60 mL) was flushed with $N_2$ and stirred at 90° C. for 16 hours. The mixture was concentrated under reduced pressure, diluted with ethyl acetate, washed sequentially with water and brine, and purified by flash chromatography (0 to 35% ethyl acetate/dichloromethane) to provide the title compound. $^1$H-NMR (DMSO-$d_6$) δ 8.82 (s, 1H), 8.05 (s, 1H), 7.64 (d, 1H), 7.50-7.53 (m, 3H), 7.20 (t, 1H), 7.14 (d, 1H), 6.81 (t, 1H), 4.45 (d, 2H), 4.00 (s, 3H), 2.70 (ddd, 2H), 1.45 (ddd, 2H), 0.97 (s, 9H).

Example 4

1-(1H-indazol-4-yl)-3-(2-isopropyl-4-(trifluoromethyl)benzyl)urea

Example 4A 2-isopropyl-4-(trifluoromethyl)benzonitrile

To a solution of 2-chloro-4-trifluoromethyl-benzonitrile (0.67 mL, 4.5 mmol) and [1,1'-bis(diphenylphosphino)ferrocene]dichloropalladium(II) (110 mg, 0.14 mmol) in 15 mL of dioxane was added Zn(iso-Propyl)$_2$ (1N in toluene, 9 mmol). The mixture was heated to reflux for 18 hours, cooled to ambient temperature and diluted with methanol. The mixture was further diluted with ether and washed sequentially with 1N HCl, water and brine. The organic layer was dried over $Na_2SO_4$, filtered, and then concentrated under reduced pressure. The crude product was purified by flash column chromatography (0% to 10% ethyl acetate/hexane) to provide the title compound. $^1$H NMR (CDCl$_3$) δ 7.73 (d, 1H), 7.63 (s, 1H), 7.55 (d, 1H), 3.45 (sept, 1H), 1.36 (d, 6H).

Example 4B (2-isopropyl-4-(trifluoromethyl)phenyl)methanamine

4-Amino-indazole-1-carboxylic acid methyl ester (1.9 g, 10 mmol) and disuccinimidylcarbonate (2.8 g, 11 mmol) were mixed in acetonitrile (100 mL) for 48 hours under nitrogen atmosphere. The solid was filtered off, washed with fresh acetonitrile (10 mL) and dried under reduced pressure at ambient temperature to provide title compound.

Example 4C 1-(1H-indazol-4-yl)-3-(2-isopropyl-4-(trifluoromethyl)benzyl)urea The title compound was obtained as outlined in Example 1D, substituting Example 4B for Example 1C: $^1$H-NMR (DMSO-$d_6$) δ 12.99 (s, 1H), 8.78 (s, 1H), 8.07 (s, 1H), 7.55-7.62 (m, 4H), 7.20 (t, 1H), 7.07 (d, 1H), 6.81 (t, 1H), 4.49 (d, 2H), 1.26 (d, 6H).

Example 5

1-(2-isopropyl-4-(trifluoromethyl)benzyl)-3-(1-methyl-1H-indazol-4-yl)urea

To a solution of Example 4C (0.468 g, 2.2 mmol) in DMF (6 mL) was added NaH (0.104 g, 2.6 mmol) and the mixture was stirred for 90 minutes. Dimethyl sulfate ($Me_2SO_4$, 0.22 mL, 2.3 mmol) was added, and the mixture was stirred for 2 hours. The mixture was diluted with ethyl acetate (1200 mL), washed sequentially with $H_2O$ (400 mL) and brine (400 mL), dried ($Na_2SO_4$), filtered, concentrated under reduced pressure, and purified by chromatography (75% diethyl ether/Hexanes to 100% diethyl ether) to provide the title compound. $^1$H-NMR (DMSO-$d_6$) δ 8.81 (s, 1H), 8.04 (s, 1H), 7.64 (d, 1H), 7.60 (s, 1H), 7.55 (m, 2H), 7.25 (t, 1H), 7.14 (d, 1H), 6.81 (t, 1H), 4.49 (d, 2H), 3.99 (s, 3H), 3.30 (m, 1H), 1.25 (d, 6H).

Example 6

Methyl 2,2-dimethyl-4-(2-((3-(1-methyl-1H-indazol-4-yl)ureido)methyl)-5-(trifluoromethyl)phenyl)butanoate

Example 6A

Methyl 4-(2-cyano-5-(trifluoromethyl)phenyl-2-2'-dimethylbut-3-ynoate

The title compounds was prepared according to the procedure outlined in Example 1A, substituting methyl 2,2-dimethylbut-3-ynoate (*J. Med. Chem.*, 1995, 38, 1831) for 3,3-dimethylbutyne. $^1$H NMR (CDCl$_3$) δ 7.79 (s, 1H), 7.77 (d, 1H), 7.62 (d, 1H), 3.81 (s, 3H), 1.64 (s, 6H).

Example 6B

Methyl 4-(2-aminomethy)-5-(trifluoromethyl)phenyl)-2,2-dimethylbutanoate

The title compounds was prepared according to the procedure outlined in Example 1B, substituting Example 6A for Example 1A. $^1$H NMR (CDCl$_3$) δ 7.46 (m, 2H), 7.38 (s, 1H), 3.94 (brs, 2H), 3.71 (s, 3H), 2.62 (quin, 2H), 1.79 (quin, 2H), 1.27 (s, 6H).

Example 6C

Methyl 2,2-dimethyl-4-(2-((3-(1-methyl-1H-indazol-4-yl)ureido)methyl)-5-(trifluoromethyl)phenyl)butanoate The title compounds was prepared according to the procedure outlined in Example 2E, substituting Example 6B for Example 2A. $^1$H NMR (DMSO) δ 8.84 (s, 1H), 8.05 (d, 1H), 7.64 (d, 1H), 7.56 (m, 3H), 7.25 (t, 1H), 7.15 (dt, 1H), 6.82 (t, 1H), 4.43 (d, 2H), 4.00 (s, 3H), 3.63 (s, 3H), 2.65 (quin, 2H), 1.76 (quin, 2H), 1.22 (s, 6H).

Example 7

1-(2-(4-Hydroxy-3,3-dimethylbutyl)-4-(trifluoromethyl)benzyl)-3-(1-methyl-1H-indazol-4-yl)urea To a mixture of Example 6C (1.16 g, 2.36 mmol) in $CH_2Cl_2$ (6 mL) at −78 C was added a solution of diisobutylaluminum hydride (1M in $CH_2Cl_2$, 6.0 mL, 6.0 mmol). The mixture was stirred cold for 2 hours, allowed to warm to ambient temperature, quenched with methanol (4 mL) and saturated aqueous Rochelle's salt (5 mL), and stirred 1 hour. The mixture was then diluted with water and extracted with 10% iPrOH in $CHCl_3$. The combined organic layer was dried ($Na_2SO_4$), filtered and concentrated under reduced pressure to provide the title compound. $^1$H NMR (DMSO) δ 8.82 (s, 1H), 8.05 (d, 1H), 7.64 (d, 1H), 7.52 (m, 3H), 7.25 (t, 1H), 7.14 (dt, 1H), 6.82 (t, 1H), 4.55 (t, 1H), 4.45 (d, 2H), 3.95 (s, 3H), 3.19 (d, 2H), 2.68 (quin, 2H), 1.45 (quin, 2H), 0.89 (s, 6H).

Example 8

2,2-dimethyl-4-(2-((3-(1-methyl-1H-indazol-4-yl)ureido)methyl)-5-(trifluoromethyl)phenyl)butanoic acid A solution of Example 6C (2.90 g, 6.09 mmol) and aqueous 1N NaOH (12.5 mL, 12.5 mmol) in 2:1 mixture of methanol and tetrahydrofuran (30 mL) was stirred at 70° C. for 4 hours, cooled to ambient temperature then acidified with 1N HCl (15 mL), diluted with water, and extracted with 10% iPrOH in $CHCl_3$. The combined organic layer was dried ($Na_2SO_4$), filtered, concentrated under reduced pressure, and triturated with diethyl ether to provide the title compound. $^1$H NMR (DMSO) δ 12.26 (brs 1H), 8.88 (s, 1H), 8.06 (d, 1H), 7.64 (d, 1H), 7.53 (m, 3H), 7.25 (t, 1H), 7.14 (d, 1H), 6.87 (t, 1H), 4.44 (d, 2H), 3.99 (s, 3H), 2.67 (quin, 2H), 1.73 (quin, 2H), 1.19 (s, 6H).

Example 9

1-[4-Chloro-3-(3,3-dimethylbutyl)benzyl]-3-(1-methyl-1H-indazol-4-yl)urea

Example 9A

3-Bromo-4-chlorobenzoic acid ethyl ester

To a solution of 3-bromo-4-chlorobenzoic acid (5.0 g, 21 mmol) in 150 mL absolute ethanol was added 15 mL of 4N HCl/dioxane. The mixture was heated to reflux for 24 hours then cooled to ambient temperature and concentrated under reduced pressure. The residue was partitioned between ethyl acetate and $H_2O$, and the separated organic phase was washed sequentially with saturated $NaHCO_3$ solution, brine, dried ($Na_2SO_4$), filtered and concentrated under reduced pressure to provide the title compound. $^1$H NMR (DMSO-$d_6$) δ 8.22 (d, 1H), 7.94 (dd, 1H), 7.80 (d, 1H), 4.33 (q, 2H), 1.33 (t, 3H); MS (DCI$^+$) m/z 263 (M+H)$^+$.

Example 9B

4-Chloro-3-(3,3-dimethylbutyl)benzoic acid ethyl ester 3,3-dimethyl-1-butylmagnesium chloride (8.00 mmol, 0.5 M THF, Platte Valley Scientific) was added dropwise to a solution of $ZnCl_2$ (4.00 mmol, IM diethyl ether, Aldrich) in 1,4-dioxane (15 mL) at ambient temperature. The mixture was stirred 30 minutes followed by addition of 3-bromo-4-chlorobenzoic acid ethyl ester (1.05 g, 3.99 mmol) and Pd(dppf)$_2$Cl$_2$ (131 mg, 0.160 mmol). The mixture was heated to reflux for 30 minutes, cooled to ambient temperature, diluted with diethyl ether and quenched with $H_2O$. The mixture was filtered through celite and the filtrate was washed with brine, dried ($Na_2SO_4$), filtered and concentrated under reduced pressure. Flash chromatography eluting with 5% to 15% ethyl acetate/hexanes provided the title compound. $^1$H NMR (DMSO-$d_6$) δ 7.89 (d, 1H), 7.78 (dd, 1H), 7.56 (d, 1H), 4.32 (q, 2H), 2.73 (m, 2H), 1.41 (m, 2H), 1.32 (t, 3H), 0.97 (s, 9H); MS (DCI$^+$) m/z 286 (M+NH$_4$)$^+$, 269 (M+H)$^+$.

Example 9C

4-Azidomethyl-1-chloro-2-(3,3-dimethylbutyl)benzene

A solution of lithium aluminum hydride (3.8 mmol, 1M THF, Aldrich) was added to 4-chloro-3-(3,3-dimethylbutyl)benzoic acid ethyl ester (1.0 g, 3.8 mmol) in 10 mL anhydrous THF at 0° C. The mixture was warmed to ambient temperature and stirred for 2 hours followed by the addition of $Na_2SO_4 \cdot 10H_2O$ (solid). The mixture was diluted with diethyl ether, filtered, and concentrated under reduced pressure. The resulting compound (0.86 g, 3.8 mmol) and diisopropylethylamine (0.97 mL, 5.6 mmol) were taken up in $CH_2Cl_2$ (15 mL) and cooled to 0° C. Methanesulfonyl chloride (0.31 mL, 4.1 mmol) was added, the mixture stirred for 2 hours, and then concentrated under reduced pressure. The residue was taken up in ethyl acetate and washed sequentially with saturated $NaHCO_3$ solution, brine, dried ($Na_2SO_4$), filtered and concentrated under reduced pressure. The crude methanesulfonate was dissolved in DMF (10 mL) followed by addition of sodium azide (0.36 g, 5.6 mmol). The mixture was heated to 65° C. for 1.5 hours, cooled to ambient temperature and concentrated under reduced pressure. The residue was taken up ethyl acetate and washed sequentially with $H_2O$, brine, dried ($Na_2SO_4$), filtered and concentrated under reduced pressure. Flash chromatography (10% ethyl acetate/hexanes) provided the title compounds. $^1$H NMR (DMSO-$d_6$) δ 7.43 (d, 1H), 7.34 (d, 1H), 7.21 (dd, 1H), 4.43 (s, 2H), 2.66 (m, 2H), 1.41 (m, 2H), 0.96 (s, 9H); MS (DCI$^+$) m/z 224 (M+H—N$_2$)$^+$.

Example 9D

4-Chloro-3-(3,3-dimethylbutyl)benzylamine

A solution of lithium aluminum hydride (3.2 mmol, 1M THF, Aldrich) was added dropwise to a solution of Example 9C (0.80 g, 3.2 mmol) in 15 mL THF at 0° C. The mixture was stirred 1 hour, quenched with $Na_2SO_4:10H_2O$, diluted with ethyl acetate, filtered, and concentrated under reduced pressure. Flash chromatography eluting with 5% to 10% methanol in dichloromethane provided the title compound. $^1$H NMR (DMSO-$d_6$) δ 7.29 (m, 2H), 7.15 (dd, 1H), 3.66 (s, 2H), 2.62 (m, 2H), 1.84 (bs, 2H), 1.40 (m, 2H), 0.96 (s, 9H); MS (DCI$^+$) m/z 243 (M+NH$_4$)$^+$, 226 (M+H)$^+$.

Example 9E

1-[4-Chloro-3-(3,3-dimethylbutyl)benzyl]-3-(1H-indazol-4-yl)urea

The title compounds was prepared according to the procedure outlined in Example 1D, substituting Example 9D for Example 1B. $^1$H NMR (DMSO-$d_6$) δ 12.98 (bs, 1H), 8.75 (s, 1H), 8.08 (s, 1H), 7.60 (d, 1H), 7.37 (d, 1H), 7.30 (d, 1H), 7.20 (m, 2H), 7.07 (m, 1H), 6.81 (t, 1H), 4.31 (d, 2H), 2.65 (m, 2H), 1.41 (m, 2H), 0.96 (s, 9H); MS (ESI$^+$) m/z 385 (M+H)$^+$.

Example 9F

1-[4-Chloro-3-(3,3-dimethylbutyl)benzyl]-3-(1-methyl-1H-indazol-4-yl)urea

Sodium hydride (41 mg, 1.0 mmol, 60% dispersion in mineral oil) was added in one portion to a solution of Example 9E (320 mg, 0.83 mmol) in DMF (8 mL) at ambient temperature. The mixture was stirred for 1.5 hours followed by the addition of dimethyl sulfate (89 μL, 0.93 mmol). The mixture was stirred 1 hour, partitioned between ethyl acetate and an aqueous NaCl solution. The separated organic layer was washed sequentially with H$_2$O, brine, dried (Na$_2$SO$_4$), filtered and concentrated under reduced pressure. Flash chromatography eluting with 4% methanol in dichloromethane provided the title compound. $^1$H NMR (DMSO-$d_6$) δ 8.77 (s, 1H), 8.04 (s, 1H), 7.63 (d, 1H), 7.37 (d, 1H), 7.33-7.10 (m, 4H), 6.80 (t, 1H), 4.31 (d, 2H), 3.99 (s, 3H), 2.65 (m, 2H), 1.41 (m, 2H), 0.95 (s, 9H); MS (ESI$^+$) m/z 399 (M+H)$^+$.

Example 10

1-(4-Chloro-3-isopropylbenzyl)-3-(1-methyl-1H-indazol-4-yl)urea

Example 10A

4-Chloro-3-isopropylbenzoic acid ethyl ester

3-Bromo-4-chlorobenzoic acid ethyl ester (1.05 g, 3.99 mmol) was added in one portion to a solution of diisopropylzinc (10.0 mmol, 1M toluene, Aldrich) in 10 mL of 1,4-dioxane followed by addition of Pd(dppf)$_2$Cl$_2$ (4.0 mmol). The mixture was heated to reflux 3 hours, cooled to ambient temperature and stirred overnight. The mixture was quenched with 1N aqueous HCl, diluted with ethyl acetate, and filtered through celite. The separated organic layer was washed sequentially with 1N aqueous HCl, brine, dried (Na$_2$SO$_4$), filtered and concentrated under reduced pressure. The residue was purified by chromatography eluting with 4% ethyl acetate/hexanes to provide the title compound. $^1$H NMR (DMSO-$d_6$) δ 7.92 (d, 1H), 7.78 (dd, 1H), 7.58 (d, 1H), 4.32 (q, 2H), 3.35 (sept, 1H), 1.32 (t, 3H), 1.24 (d, 6H).

Example 10B

4-Azidomethyl-1-chloro-2-isopropylbenzene

The title compounds was prepared according to the procedure outlined in Example 9C, substituting Example 10A for Example 9B. $^1$H NMR (DMSO-$d_6$) δ 7.44 (d, 1H), 7.40 (d, 1H), 7.22 (dd, 1H), 4.46 (s, 2H), 3.31 (sept, 1H), 1.22 (m, 6H); MS (DCI$^+$) m/z 182 (M+H—N$_2$)$^+$.

Example 10C

4-Chloro-3-isopropylbenzylamine

The title compounds was prepared according to the procedure outlined in Example 9D, substituting Example 10B for Example 9C. $^1$H NMR (DMSO-$d_6$) δ 7.35 (d, 1H), 7.31 (d, 1H), 7.16 (dd, 1H), 3.68 (s, 2H), 3.29 (sept, 1H), 1.83 (bs, 2H), 1.21 (m, 6H).

Example 10D 1-(4-Chloro-3-isopropylbenzyl)-3-(1H-indazol-4-yl)urea

The title compounds was prepared according to the procedure outlined in Example 1D, substituting Example 10C for Example 1B. $^1$H NMR (DMSO-$d_6$) δ 12.97 (bs, 1H), 8.82 (s, 1H), 8.12 (s, 1H), 7.61 (d, 1H), 7.38 (m, 2H), 7.20 (m, 2H), 7.07 (d, 1H), 6.90 (t, 1H), 4.35 (d, 2H), 3.31 (sept, 1H), 1.22 (d, 6H); MS (ESI$^+$) m/z 343 (M+H)$^+$.

Example 10E 1-(4-Chloro-3-isopropylbenzyl)-3-(1-methyl-1H-indazol-4-yl)urea

The title compounds was prepared according to the procedure outlined in Example 9F, substituting Example 10D for Example 9E. $^1$H NMR (DMSO-$d_6$) δ 8.79 (s, 1H), 8.05 (s, 1H), 7.63 (d, 1H), 7.38 (m, 2H), 7.30-7.10 (m, 3H), 6.81 (t, 1H), 4.34 (d, 2H), 3.99 (s, 3H), 3.31 (sept, 1H), 1.22 (d, 6H); MS (ESI$^+$) m/z 356 (M+H)$^+$.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:
1. A compound of formula (I)

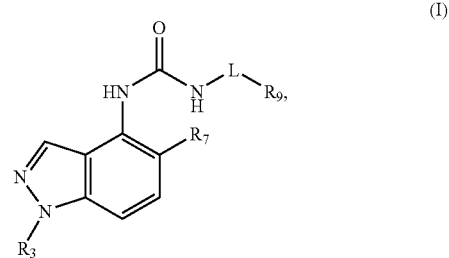

or a pharmaceutically acceptable salt or thereof, wherein
L is CH$_2$;
R$_3$ is methyl (CH$_3$);

$R_7$ is hydrogen; and
$R_9$ is phenyl;
with the proviso that the following compounds are excluded:
N-(4-chlorobenzyl)-N'-(1-methyl-1H-indazol-4-yl)urea,
N-(4-tert-butylbenzyl)-N'-(1-methyl-1H-indazol-4-yl) urea,
N-(3fluoro-4-(trifluoromethyl)benzyl)-N'-(1-methyl-1H-indazol-4yl)urea,
N-(4fluoro-3-(trifluoromethyl)benzyl)-N'-(1-methyl-1H-indazol-4-yl)urea,
N-(3,4-dichlorobenzyl)-N'-(1-methyl-1H-indazol-4-yl)urea,
N-(2,4-dichlorobenzyl)-N'-(1-methyl-1H-indazol-4-yl)urea,
N-(4-ethylbenzyl)-N'-(1-methyl-1 H-indazol-4-yl)urea,
N-(2-chlorobenzyl)-N'-(1-methyl-1H-indazol-4-yl)urea,
N-(4-fluorobenzyl)-N'-(1-methyl-1H-indazol-4-yl)urea,
N-(2-fluorobenzyl)-N'-(1-methyl-1H-indazol-4-yl)urea,
N-[1-(4-bromophenyl)ethyl]-N'-(1methyl-1H indazol-4yl)urea, and
N-(1-methyl-1H-indazol-4yl)-N'-{4-1[(trifluoromethyl)thio]benzyl }urea and wherein the
$R_9$ phenyl is substituted with 2 substituents independently selected from the group consisting of alkoxycarbonylalkyl, alkyl, carboxyalkyl, and hydroxyalkyl.

2. A compound of formula (I)

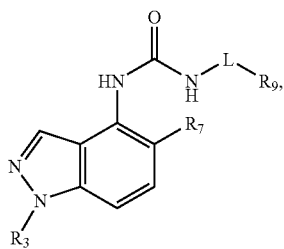

or a pharmaceutically acceptable salt or thereof, wherein
L is $CH_2$;
$R_3$ is methyl ($CH_3$);
$R_7$ is hydrogen; and
$R_9$ is aryl;
with the proviso that the following compounds are excluded:
N-(4-chlorobenzyl)-N'-(1-methyl-1H-indazol-4-yl)urea,
N-(4-tert-butylbenzyl)-N'-(1-methyl-1H-indazol-4-yl) urea,
N-(3-fluoro-4-(trifluoromethyl)benzyl)-N'-(1-methyl-1H-indazol-4yl)urea,
N-(4-fluoro-3-(trifluoromethyl)benzyl)-N'-(1-methyl-1H-indazol-4yl)urea,
N-(3,4-dichlorobenzyl)-N'-(1-methyl-1H-indazol-4-yl) urea,
N-(2,4-dichlorobenzyl)-N'-(1-methyl-1H-indazol-4-yl) urea,
N-(4-ethylbenzyl)-N'-(1-methyl-1H-indazol-4-yl)urea,
N-(2-chlorobenzyl)-N'-(1-methyl-1H-indazol-4-yl)urea,
N-(4-fluorobenzyl)-N'-(1-methyl-1H-indazol-4-yl)urea,
N-(2-fluorobenzyl)-N'-(1-methyl-1H-indazol-4-yl)urea,
N-[1-(4-bromophenyl)ethyl]-N'-(1-methyl-1H-indazol-4-yl)urea, and
N-(1-methyl-1H-indazol-4-yl)-N'-{4-1[(trifluoromethyl)thio]benzyl}urea,
wherein said compound does not inhibit Cytochrome P450 3A4 enzyme (CYP3A4) in vitro and in vivo.

3. A compound of having the general formula (I)

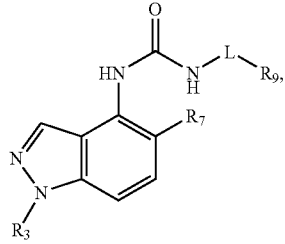

or a pharmaceutically acceptable salt or thereof, wherein
L is $CH_2$;
$R_3$ is methyl ($CH_3$);
$R_7$ is hydrogen; and
$R_9$ is aryl;
with the proviso that the following compounds are excluded:
N-(4-chlorobenzyl)-N'-(1-methyl-1H-indazol-4-yl)urea,
N-(4-tert-butylbenzyl)-N'-(1-methyl-1H-indazol-4-yl) urea,
N-(3-fluoro-4-(trifluoromethyl)benzyl)-N'-(1-methyl-1H-indazol-4-yl)urea,
N-(4-fluoro-3-(trifluoromethyl)benzyl)-N'-(1methyl-1H-indazol-4-yl)urea,
N-(3,4-dichlorobenzyl)-N'-(1-methyl-1H-indazol-4-yl )urea,
N-(2,4-dichlorobenzyl)-N'-(1-methyl-1H-indazol-4-yl )urea,
N-(4-ethylbenzyl)-N'-(1-methyl-1H-indazol-4-yl)urea,
N-(2-chlorobenzyl)-N'-(1-methyl-1H-indazol-4-yl)urea,
N-(4-fluorobenzyl)-N'-(1-methyl-1H-indazol-4-yl)urea,
N-(2-fluorobenzyl)-N'-(1-methyl-1H-indazol-4-yl)urea,
N-[1-(4-bromophenyl)ethyl]-N'-(1-methyl-1H -indazol-4-yl)urea, and
N-(1-methyl-1H-indazol-4-yl)-N'-{4-1[(trifluoromethyl)thio]benzyl}urea and,
wherein the compound is:
1-(2-(3,3-dimethylbutyl)-4-(trifluoromethyl)benzyl)-3-(1-methyl-1H-indazol-4-yl)urea; or a pharmaceutically acceptable salt thereof.

4. A compound of general formula 1-(2-(3,3-dimethylbutyl)-4-(trifluoromethyl)benzyl)-3-(1-methyl-1H-indazol-4-yl)urea; or a pharmaceutically acceptable salt thereof.

5. A pharmaceutical composition comprising a therapeutically effective amount of a compound of formula (I) according to any one of claims 1, 2, 3 or 4, or a pharmaceutically acceptable salt thereof and a pharmaceutically acceptable carrier.

6. The pharmaceutical composition according to claim 5 wherein the compound is 1-(2-(3,3-dimethylbutyl)-4-(trifluoromethyl)benzyl)-3-(1-methyl-1H-indazol-4-yl)urea or a pharmaceutically acceptable salt thereof, and a pharmaceutically acceptable carrier.

7. A pharmaceutical composition comprising a compound of formula (I) according to any one of the claims 1, 2, 3, 5, 6 or 4 or a pharmaceutically acceptable salt thereof, one or more nonsteroidal anti-inflammatory drug, and a pharmaceutically acceptable carrier.

* * * * *

UNITED STATES PATENT AND TRADEMARK OFFICE
CERTIFICATE OF CORRECTION

PATENT NO. : 7,767,705 B2  
APPLICATION NO. : 11/844712  
DATED : August 3, 2010  
INVENTOR(S) : Lee et al.

Page 1 of 1

It is certified that error appears in the above-identified patent and that said Letters Patent is hereby corrected as shown below:

Column 31, line 8, claim 1: "N-(3fluoro" to read as --N-(3-fluoro--

Column 31, line 10, claim 1: "N-(4fluoro" to read as --N-(4-fluoro--

Column 31, line 16, claim 1: "(1-methyl-1 H" to read as --(1-methyl-1H--

Column 31, line 20, claim 1: "(1methyl-1H  indazol" to read as --(1-methyl-1H-indazol--

Column 31, line 22, claim 1: "indazol-4yl)" to read as --indazol-4-yl)--

Column 31, line 23, claim 1: "benzyl }" to read as --benzyl}--

Column 31, line 52, claim 2: "indazol-4yl" to read as --indazol-4-yl--

Column 31, line 54, claim 2: "indazol-4yl" to read as --indazol-4-yl--

Column 32, line 3, claim 3: "A compound of having" to read as --A compound having--

Column 32, line 29, claim 3: "(1methyl" to read as --(1-methyl--

Column 32, line 39, claim 3: "(1-methyl-1H  -indazol" to read as --(1-methyl-1H-indazol--

Column 32, line 63, claim 6: "drug," to read as --drugs,--

Signed and Sealed this  
Eighth Day of March, 2011

David J. Kappos  
*Director of the United States Patent and Trademark Office*